United States Patent
Abdullah

(10) Patent No.: US 11,731,887 B2
(45) Date of Patent: Aug. 22, 2023

(54) METHOD FOR THE DESALINATION OF SEAWATER USING SOLAR ENERGY

(71) Applicant: Ali Fadlelmula Mohamed Ali, Hofuf (SA)

(72) Inventor: Mohammad Suliman Shathele Abdullah, Hofuf (SA)

(73) Assignee: Ali Fadlelmula Mohamed Ali, Hofuf (SA)

( * ) Notice: Subject to any disclaimer, the term of this patent is extended or adjusted under 35 U.S.C. 154(b) by 104 days.

(21) Appl. No.: 16/746,223

(22) Filed: Jan. 17, 2020

(65) Prior Publication Data

US 2021/0221708 A1  Jul. 22, 2021

(51) Int. Cl.
| | |
|---|---|
| *C02F 103/08* | (2006.01) |
| *C12P 17/18* | (2006.01) |
| *B01D 61/36* | (2006.01) |
| *C02F 1/44* | (2023.01) |
| *C12N 1/14* | (2006.01) |

(52) U.S. Cl.
CPC ............ *C02F 1/447* (2013.01); *B01D 61/364* (2013.01); *B01D 61/366* (2013.01); *C12N 1/14* (2013.01); *C12P 17/182* (2013.01); *B01D 2311/12* (2013.01); *B01D 2313/22* (2013.01); *C02F 2103/08* (2013.01); *C02F 2305/00* (2013.01)

(58) Field of Classification Search
CPC .... C02F 1/04; C02F 2103/08; B01D 2311/12; B01D 2313/22; Y02P 20/133
See application file for complete search history.

(56) References Cited

U.S. PATENT DOCUMENTS

| | | | | |
|---|---|---|---|---|
| 3,198,713 | A * | 8/1965 | McCormick | ........... C12M 23/10 206/509 |
| 4,329,205 | A * | 5/1982 | Tsumura | ................... C02F 1/14 203/DIG. 1 |
| 2014/0329073 | A1* | 11/2014 | Barshilia | ............. C23C 14/5873 428/457 |
| 2018/0043278 | A1* | 2/2018 | Singamaneni | ....... B01D 1/0035 |

OTHER PUBLICATIONS

Arunkumar, T., et al. "Experimental study on various solar still designs." International Scholarly Research Notices 2012 (2012). (Year: 2012).*

(Continued)

*Primary Examiner* — Bradley R Spies
(74) *Attorney, Agent, or Firm* — Bay State IP, LLC

(57) ABSTRACT

A technique to desalinate seawater using melanin-concentrated solar energy wherein the melanin is extracted from a local isolate *Aspergillus niger*. A device consists of two fixed upper and lower containers with same volume of seawater in both, with or without melanin powder dissolved in the lower container at rate of 0.17 gm of melanin powder per 10 ml of water. The device is put outdoors under direct sunlight during daytime, circular water droplets free of salt starts to appear on the external bottom of upper container. Water droplets are collected by a sterile glass rod, pH of droplets water is about 7.1. Yield of fresh water is approximately 10 ml droplets water from 600 ml seawater per hour; after 24 hours day and night incubation, seawater in the upper container dries out leaving salt crystals. Yield of 1000 m3 seawater is 100 m3 freshwater (1000 L seawater yield 100 L freshwater).

4 Claims, 4 Drawing Sheets

(56) References Cited

OTHER PUBLICATIONS

Cappelletti, Giulio Mario. "An experiment with a plastic solar still." Desalination 142.3 (2002): 221-227. (Year: 2002).*

Zong, Lu, Mingjie Li, and Chaoxu Li. "Intensifying solar-thermal harvest of low-dimension biologic nanostructures for electric power and solar desalination." Nano Energy 50 (2018): 308-315. (Year: 2018).*

Solar Still Challenge—Global experiment for the International Year of Chemistry—2011 (Year: 2011).*

* cited by examiner

METHOD FOR THE DESALINATION OF SEAWATER USING SOLAR ENERGY

BACKGROUND OF THE INVENTION

Field of the Invention

The invention herein relates to a method of desalination of seawater to produce freshwater using solar energy only.

Description of the Related Art

*Aspergillus niger* complex contains imperfect saprophytic black mycelial fungi ubiquitous in nature that reproduce asexually with production of conidia (fungal spores). In a comparative study of five *Aspergillus* species, it was reported that the maximum amount of melanin was obtained from *A. niger* (Pal et al., 2014). Melanin is macromolecule formed by oxidative polymerization of phenolic or indolic compounds. Often the resulting pigments are brown or black in color but many other colours have also been observed. Chemically, melanin is negatively charged, hydrophobic macromolecule with amorphous nature. Melanin is synthesized in living organisms by oxidative polymerization of various phenolic substances in the process of adaptation (Sajjan, 2010). Naturally, melanin protect against UV and visible light, as charge transport mediators, free-radical scavengers, antioxidants, metal ion balancers beside other functions (Geng et al., 2010). The discovery of the property of melanin to dissociate and re-form the water molecule using the entire electromagnetic spectrum (Herrera et al., 2010) may pave the way for utilizing the produced energy. In this manner melanin may act as a light antenna, collecting numerous photons, then that concentrated energy could drive metabolic processes. Photoreceptor molecules that absorb particular wavelengths of light have been reported in fungi (Isaac, 1995). Turick et al. (2011) demonstrated that microbial melanin is oxidized in the presence of gamma radiation; sustained oxidation resulted in production of electric current which is pronounced in presence of a reductant.

Distillation is the oldest method for making freshwater from salt water. Salt water is boiled then the steam is passed through a condensing tube. The method has been used for centuries, but it is energy inefficient as more than half the cost of operation is for energy. With the progress of technological know-how in modern times, a number of techniques has been used for seawater desalination. Osmosis desalination systems are based on osmosis, and depend on differences of two solvents' concentration separated by semi-permeable membranes. The actual movement of solvent molecules depends also on the pressures on fluids at the two sides of the semi-permeable membrane. In reverse osmosis (RO), sufficient pressure in excess of the osmotic pressure is applied to the fluid where the solute concentration is smaller at the side of the semi-permeable membrane. Then a reverse movement of the fluid of higher solution concentration through the semi-permeable membrane into a fluid of low solution concentration, takes place. RO utilizes pressure as a driving force to move the saline solution through a semi-permeable membrane (Crittenden, 2005) to separate the solutes from the seawater. The energy consumption for RO distillation of seawater is in the range of 3-5.5 kWh m-3 (Desware, 2014). There are many studies of the use of solar energy (SE) for RO by using photovoltaic (PV) electrical generators or by pressurization energy from solar-thermal concentrator systems (Sampathkumar, 2010). In the USA, Europe and some other countries, the prevailing desalination technology is seawater reverse osmosis (SWRO) with its high energy demand. A large amount of water is desalinated daily, in the Kingdom of Saudi Arabia (KSA) by energy-intensive technology as multi-stage flash distillation (MSF) (Ghaffour et al., 2013).

The Paris Agreement on Climate Change, which aims to limit global warming by significantly decarbonising human activity stressed utilization of renewable energy in order to preserve the planet and humanity (UNFCCC, 2015). Renewable energy resources and technologies have an important role in achieving this goal. Desalination by using renewable energy such as SE is considered suitable; there are many places in the world where abundant supply of solar energy is available. As well, in such places as deserts, there is a great demand for fresh water. In KSA, availability of SE makes it a fascinating tool to explore cost-effective technologies for seawater desalination. The National Initiative for Solar Desalination, is a joint initiative of King Abdulaziz City for Science and Technology (KACST) with IBM. Al-Khafji plant has a total of 30,000 m3/day being desalinated by 10 MW of SE (Ghaffour et al., 2013). Adsorption desalination (AD) is a new low-energy desalination process which can be driven by waste heat or SE. The inherent component of the AD process is silica gel, which adsorbs seawater to be then desorbed at a low temperature (55 to 85° C.) provided by SE, and later condensed free of salts. It was demonstrated that AD energy consumption may be <1.5 kWh/m3 (Ng et al., 2013). Although its energy consumption is less than other conventional methods, yet using SE is faced by the drawback of the diurnal pattern of sunlight. Membrane distillation (MD) is a method where a hydrophobic membrane is used to separate the heated seawater by allowing transport of the vapour only through its micropores. The vapour is driven by difference in vapour pressure on both sides of the membrane where it condenses on the cooler side and produces water (Al-Saadi et al., 2013). Other researchers developed Nanophotonics-enabled solar membrane distillation" technology (NESMD). It utilizes manufactured nanoparticles, which can convert sunlight into heat for seawater heating as demonstrated by a trial. The group used NESMD small chamber and managed to get a water production rate of about 6 liters (1.3 gallons) per meter squared per hour.

By infrared spectroscopy to study hydrogen bonding strength in intracellular water, it was demonstrated that liquid water exists in two distinct structural forms. The study revealed existence of only two distinct hydrogen bond strengths i.e. two types of water structurally i.e. water exists as networks of molecules interconnected by hydrogen bonds (Wiggins and van Ryn, 1986). Theory of co-existence of microdomains of different densities shows that H atom lies on a straight line between two O atoms, keeping molecules apart and water less dense, in a structured form of low density water (LDW). The other form, where H bonds are weak bent allowing molecules to approach each other and increase density, is non-structured high density water (HDW). The important difference from classical osmotic theory is that in two-state water pressure gradients displace the water equilibrium, either inducing HDW where the pressure is positive and/or inducing LDW where the pressure is negative.

Both ions of a neutral salt must occupy the same type of microdomain determined by the relative potencies of the individual ions as chaotropes or kosmotropes. For example, $CaSO_4$ is sparingly soluble partly because both $Ca^{2+}$ and $SO_4^{2-}$ are potent kosmotropes, requiring a large displacement of the water equilibrium. $CaCl_2$, on the other hand is highly soluble, partly because $Cl^-$ is a chaotrope, so that the displacement of the water equilibrium by $Ca^{2+}$ is corrected by an opposite displacement by $2Cl^-$. It turns out that both $CaCl_2$ and $CaSO_4$ partition into HDW but $CaSO_4$ much more strongly than $CaCl_2$(Wiggins, 2008).

The fixed charges on biopolymers are always strong chaotropes (large univalent anionic or cationic groups), inducing HDW in the double layer. When the counter-ion is also a chaotrope the cumulative effect is such that water adjacent to the surface appears to become pure HDW and compensation for the pressure gradient consists predominantly in induction of LDW.

For example cations show a preference for LDW in the order: $Cs^+>K^+>Na^+>Li^+>H^+$. The break occurs between $K^+$ and $Na^+$; i.e. $K^+$ is a chaotrope and $Na^+$ is a kosmotrope. Univalent anions show the same trends. Their order is $I^->Br^->Cl^->F^-$. Here, the break is between $Cl^-$ and $F^-$. The only differences between the ions on either side of the break is size. In NaCl, $Na^+$ is a kosmotrope and Cl is a chaotrope, so the displacement of water equilibrium by $Na^+$ is corrected by opposite displacement by $Cl^-$ leading to induction of LDW formation.

Hydrophobic molecules and small cations such as $Na^+$, $Li^+$, $H^+$, $Ca^{2+}$, $Mg^{2+}$ have an affinity for high density water (HDW), it will attract some HDW to its surface, increasing the amount of HDW. On the other hand most anions has an affinity for low density water (LDW) but cannot generate LDW immediately at the surface because that region is under positive pressure. It follows that water immediately adjacent to a surface is always HDW, irrespective of the particular properties of the surface.

Various techniques to desalinize water are directed towards exploring RE because the main drawback of conventional methods is the high consumption of energy. In the KSA, MSF distillation consumption is >10 kWh per m3 of desalinated water and in other countries SWRO, the technology of choice, is energy intensive as well (3-4 $kWh/m_3$). Furthermore, implication of both techniques in environmental issue is great by emission of greenhouse gases (GHGs). Some of the reviewed methods above that utilize RE, employed complicated pathways to reach the final product although still more research is going on to obtain efficient items to the process. Therefore simple green methods to serve small rural communities off of the grid could prove to be cost-effective in light of availability of SE in the KSA.

SUMMARY OF THE INVENTION

The present invention relates to a method of desalination of seawater in which there is propagation of a local isolate *Aspergillus niger* in appropriate culture media and then extraction of melanin. The extraction process uses chemicals to obtain melanin in dry form. The obtained melanin can be used to concentrate SE for seawater desalination.

Melanin is demonstrated to dissociate and re-form the water molecule by absorption of the entire electromagnetic spectrum producing energy; however, in the present invention it appears that sole SE played a major role. Making use of the fact that ordinary bulk water exists in two kinds: HDW and LDW prompted us to think of the present invention. For instance, in the upper container the positively-charged HDW lies in upper position and towards the container's bottom lies the negatively-charged LDW. So a device was arranged to consist of a lower container and fixed above it an upper container where the same conditions prevail in both. Hence, the positively-charged HDW ions in the lower container attracted the negatively-charged LDW ions in the upper container through the bottom of the upper container that function as filter to provide fresh droplets water free of solute. Beside the power of "unlike poles attract" that induce emerging of circular water droplets through glass or plastic material in the bottom of the upper container, in the present invention, may be interpreted by the "quantum tunneling state" of the water. Discovery of this state of water contributes to the knowledge of utilization of energy by water. It has been reported that quantum tunneling allows particles to move through energy barriers and verified using neutron scattering technology (Kolesnikov et al., 2016).

For collection of droplet water, some innovative approaches to change design of the outer surface of the base of upper container could be used to render the process efficient and continuous.

To achieve the above purpose, in one embodiment, the fungal strain is cultured on a solid medium wherein growth is collected, then treated with chemicals and heated, then melanin is precipitated by chemicals and dried.

Wherein the agar medium is incubated at 30° C. for 14 days, cut in disks and heated in a solution until boiling, then heated in a heating apparatus and precipitated in a chemical.

The disks of 15 mm diameter, the solution is 1 M sodium hydroxide 3 ml, the heating apparatus is autoclave, the heating temperature is 121° C., the heating time is 20 minutes.

The alkaline solution obtained is precipitated with hydrochloric acid, washed 3 times in DW and dried overnight at 20° C.

In one embodiment, in bench scale experiment, a method of desalination of seawater according to the present disclosure, after lots of preliminary experiments, consists of the following steps:

1. Glass Petri dishes consists of two plates of same size where volume of 30 ml seawater was put in each, and gently arranged as upper and lower plates.

2. A weight of 0.17 gm of melanin powder per 10 ml of water was dissolved in the lower plate as arranged in step 1.

3. The device assembled in step 2 was put on bench near a window to be exposed to sun rays and sunlight at room temp. After about 30 mins water droplets started to appear on the lower face of the upper plate and increased in size as time passes.

4. Water droplets obtained in step 3 were collected by a sterile glass rod in a beaker to measure its volume.

In one embodiment, rounded plastic containers were used consist of two plates of same size where volume of 600 ml seawater was put in each, gently arranged as upper and lower plates with melanin and put outdoors exposed to sunlight. After 48 hours, seawater in upper plate dried out leaving salt crystals while in the lower container seawater was about 500 ml at experiment termination.

In another embodiment, plastic containers were used consists of two plates of same size where volume of 600 ml seawater was put in each, gently arranged as upper and lower plates without melanin and put outdoors exposed to sunlight. After 48 hours, seawater in upper plate still moist and needed further 4 hours to dry out while in the lower container seawater was about 450 ml at experiment termination.

The droplet water obtained according to the present disclosure was at a rate of approximately 10 ml droplets water from 600 ml seawater per hour i.e. 1000 $m_3$ yield 100 $m_3$ (1000 L seawater yield 100 L freshwater). The difference in droplets water yield with and without melanin is not significant. pH of droplets water is about 7.1.

As compared to other methods of water desalination, embodiments in the present disclosure have the following advantages:

1. Consumption of energy is low as it utilizes SE in all reactions till production of freshwater.
2. It is simple and does not require complex infrastructure or sophisticated equipment.
3. An off-grid technology to provide families in rural regions with fresh drinking water.
4. The technique can be scaled up for larger regions.
5. A green method with no greenhouse gases emission.
6. The problem of diurnal pattern of sunlight is solved as energy of infrared rays continues during night.
7. It does not require pre-treatment of seawater.

The details of one or more embodiments of the present invention are presented in the accompanying figures and the description below. Other features, objects, and advantages of the invention will be apparent from the description and figures and from the claims.

DETAILED DESCRIPTION OF THE SEVERAL EMBODIMENTS

Figure 1:
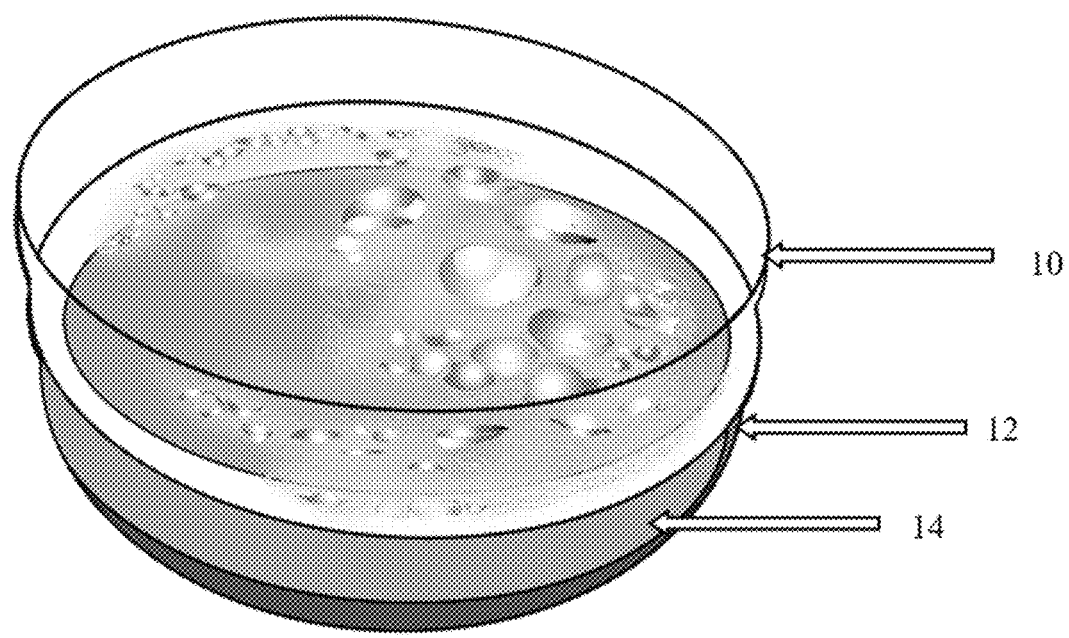
FIG. 1 illustrates bench scale experiment of two glass Petri dishes fixed one over the other with melanin dissolved in the lower dish and the device is exposed to sunlight according to embodiment 3.
Figure 2:
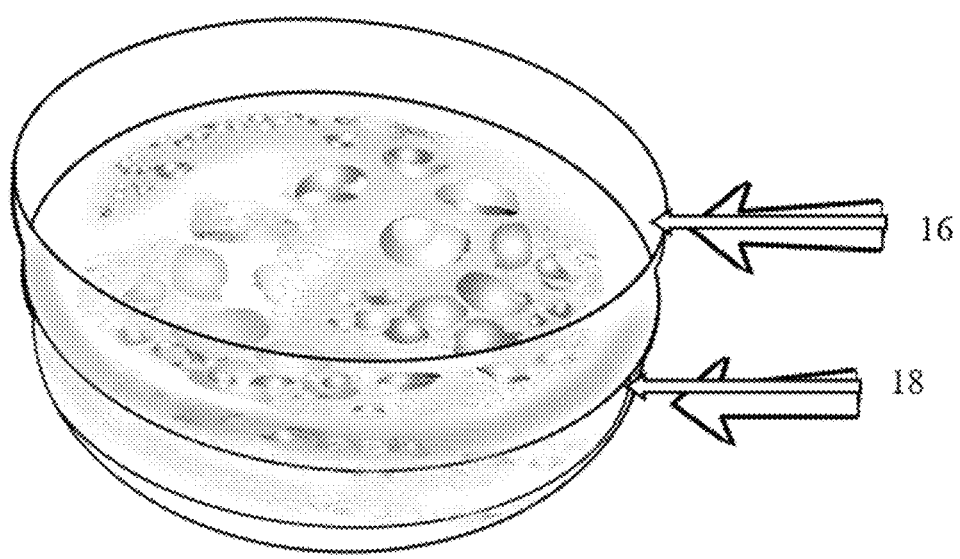
FIG. 2 illustrates another bench scale experiment of two glass Petri dishes fixed one over the other and the device is exposed to sunlight according to embodiment 4.
Figure 3:
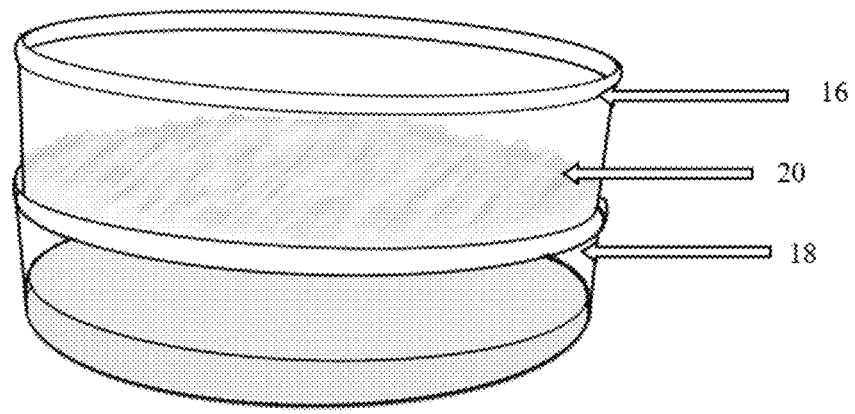
FIG. 3 illustrates bench scale experiment showing two glass Petri dishes fixed one over the other with salt crystals in the upper dish according to embodiment 4.
Figure 4:
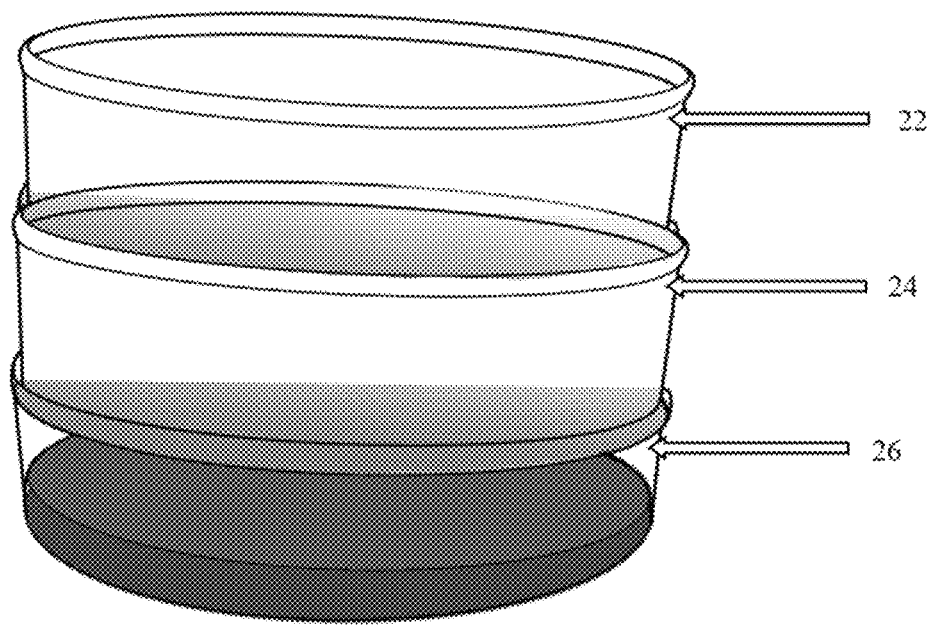
FIG. 4 illustrates another bench scale experiment of three glass Petri dishes fixed one over the other and the device is exposed to sunlight according to embodiment 5.
Figure 5:
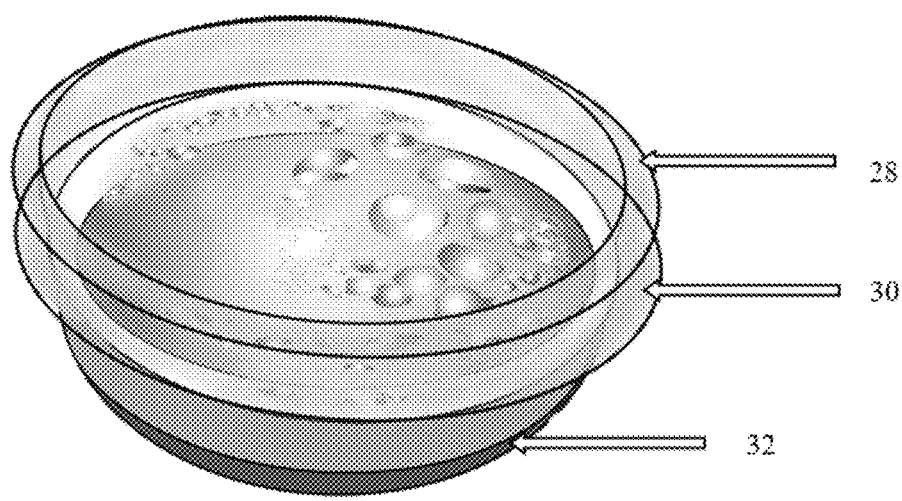
FIG. 5 illustrates an outdoor experiment of two rounded plastic containers fixed one over the other with melanin dissolved in the lower container and the device is placed outdoors to be exposed to direct sunlight according to embodiment 6.
Figure 6:
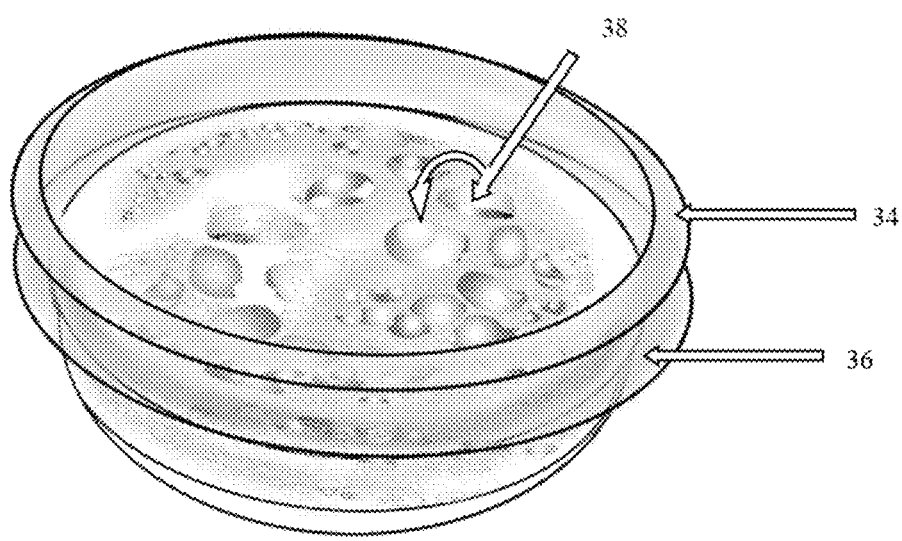
FIG. 6 illustrates an outdoor experiment of two rounded plastic containers fixed one over the other and the device is placed outdoors to be exposed to direct sunlight according to embodiment 7.
Figure 7:
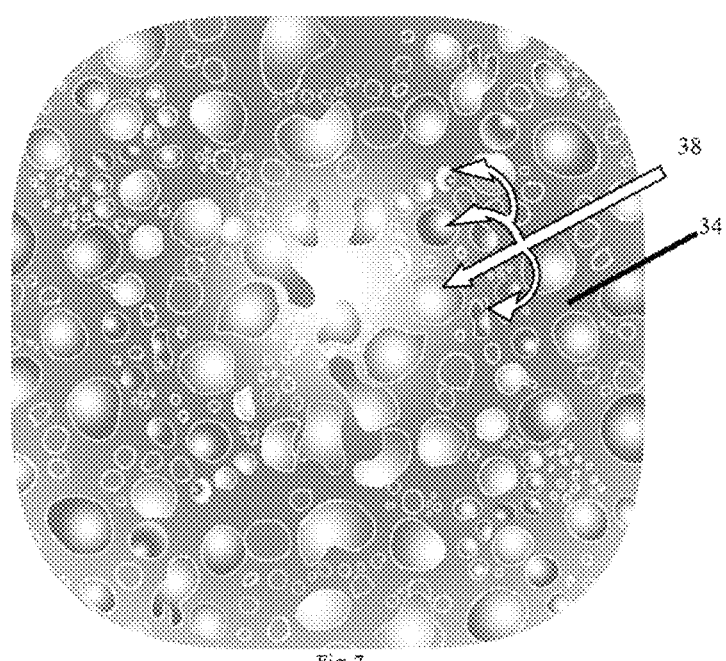
FIG. 7 illustrates an outdoor experiment of two rounded plastic containers fixed one over the other showing formation of circular water droplets on the lower surface of the upper container according to embodiment 7.

To make the present disclosure clear, the following embodiments give detailed description.

Embodiment 1

Prepare Sabouraud's agar (Oxoid, UK) on disposable plastic Petri dishes, make subcultures from *A. niger* stock and incubate at 30° C. for 14 days. Prepare wet mount smears by removing portions of the mycelia and stain with lacto-phenol cotton-blue. Examine microscopically to confirm pure growth of the mould.

Embodiment 2

To extract melanin from the obtained culture, cut from agar surface disks of 15 mm diameter and heat in 1 M sodium hydroxide 3 ml volume until boiling. Then heat in autoclave, at temperature of 121° C., for 20 minutes. Treat the solution with hydrochloric acid to precipitate melanin, wash 3 times in DW and dry overnight at 20° C.

Embodiment 3

In a bench scale experiment, put 30 ml seawater as such without any treatment in each of two glass Petri dishes and fix one over the second to make an upper petri dish 10 and a lower petri dish 12. Dissolve 0.17 gm of melanin powder per 10 ml water 14 in the lower plate. Place the device beside a window to be exposed to sunlight. On examination the lower surface of the upper plate after 30 minutes is cloudy and buildup of water droplets starts and is increased as time passes. Collect water droplets with sterile glass rod to measure its volume.

Embodiment 4

In another bench scale experiment, put 30 ml seawater as such without any treatment in each of an upper petri dish 16 and a lower petri dish 18 and fix one over the second to make upper 16 and lower plates 18. Place the device beside a window to be exposed to sunlight. On examination the lower surface of the upper plate after 30 minutes is cloudy and buildup of water droplets starts and is increased as time passes. Collect water droplets with sterile glass rod to measure its volume. The buildup of water droplets starts immediately after collection; after 24 hours water dries out in the upper dish leaving salt crystals only 20.

Embodiment 5

Further, in another bench scale experiment, put 30 ml seawater as such without any treatment in each of three glass Petri dishes and fix one over the other to make an upper petri dish 22, a middle petri dish 24 and a lower petri dish 26. Dissolve 0.17 gm of melanin powder per 10 ml water in the lower plate. Place the device beside a window to be exposed to sunlight. On examination the lower surface of the upper and middle plates after 30 minutes is cloudy and buildup of water droplets starts and is increased as time passes. Collect water droplets from the upper and middle plates with sterile glass rod to measure its volume. The water volume is double the volume obtained in embodiment 3.

Embodiment 6

In an outdoor experiment, use rounded plastic containers of same size where volume of 600 ml seawater is put in each. Arrange as an upper plate 28 and a lower plate 30. Dissolve 0.17 gm of melanin powder 32 per 10 ml of water in the lower plate. Place the device outdoors to be exposed to direct sunlight. Collect water droplets with glass rod. After 24 hours, seawater in upper plate is dried out while in lower container seawater is about 500 ml at the end of experiment. Collected droplet water after 24 hours is 100 liter from 1000 liter seawater i.e. 100 $m_3$ from 1000 $m_3$ seawater (1 $m_3$ seawater gives 16 L per hour).

Embodiment 7

In another outdoor experiment, use rounded plastic containers of same size where volume of 600 ml seawater is put in each. Arrange as an upper plate 34 and a lower plate 36 without melanin. Place the device outdoors to be exposed to direct sunlight. Collect water droplets 38 with glass rod. After 24 hours, seawater in upper plate is dried out while in lower container seawater is about 450 ml at the end of experiment. Difference between collected droplet water after 24 hours in embodiment 5 (using melanin) and embodiment 6 (without melanin) is not significant.

REFERENCES

Al-Saadi A, Ghaffour N, Li J D, Gray S, Francis L, Maab H, Nunes S, Amy G. (2013). Modeling of air-gap membrane distillation process: A theoretical and experimental study. Journal of Membrane Science; 445: 53-65.

Crittenden, John; Trussell, Rhodes; Hand, David; Howe, Kerry and Tchobanoglous, George. (2005). Water Treatment Principles and Design, Edition 2. John Wiley and Sons. New Jersey. ISBN 0471110183

Desware, (2014). Encyclopedia of Desalination and Water Resources. Energy requirements of desalination processes, www.desware.net/desa4.aspx Geng, J., Yuan, P., Shao, C., Yu, S. B., Zhou, B., Zhou, P., Chen, X. D. (2010). Bacterial melanin interacts with double-stranded DNA with high affinity and may inhibit cell metabolism in vivo. Arch. Microbiol. 192, 321-329.

Ghaffour N, Missimer T M, Amy G L. (2013). Technical review and evaluation of the economics of water desalination: Current and future challenges for better water supply sustainability. Desalination; 309: 197-207.

Herrera, A. S., Esparza, M. C., Arias, R. I. S., Arias, P. E. S, Arias, M. P. S. (2010). The unexpected capacity of melanin to dissociate the water molecule fills the gap between the life before and after ATP. Biomed Res. 21(2):224-6.

Isaac, S. (1995). Moulds, mildews and other fungi are often found in shaded and dark situations—Is their development influenced by light? Mycologist. Vol. 9, Part 1, 41-42.

Kolesnikov A. I., Reiter G. F., Choudhury N. et al. (2016). Quantum Tunneling of Water in Beryl: A New State of the Water Molecule. Phys. Rev. Lett. 116, 167802. Ng K C, Thu K, Kim Y D, Chakraborty A, Amy G. (2013). Adsorption desalination: An emerging low-cost thermal desalination method Desalination; 308: 161-179.

Pal A. K, Gajjar D. U., Vasavada A. R. (2014). DOPA and DHN pathway orchestrate melanin synthesis in *Aspergillus* species. Med Mycol. 52(1), 10-8. doi:10.3109/13693786.2013.826879.

Sajjan, S. (2010). Purification and physiochemical characterization of melanin pigment from *Klebsiella* sp. GSK. J. Microbiol. Biotechnol. 20, 1513-1520.

Sampathkumar, K., T. V. Arjunan, P. Pitchandi, P. Senthilkumar. (2010). Active solar distillation—A detailed review, Renewable and Sustainable Energy Reviews, Volume 14, Issue 6, Pages 1503-1526.

Turick, C. E., Ekechukwu, A. A., Milliken, C. E., Casadevall, A., Dadachova, E. (2011). Gamma radiation interacts with melanin to alter its oxidation-reduction potential and results in electric current production. Bioelectrochemistry. 82(1), 69-73. DOI: 10.1016/j.bioelechem.2011.04.009

UNFCCC. (2015). Report of the Conference of the Parties on its twenty-first session, held in Paris from 30 Nov. to 13 Dec. 2015. Addendum-Part Two Action Task by Conf. Parties; 1194:1-36.

Wiggins P (2008) Life Depends upon Two Kinds of Water. PLoS ONE 3(1): e1406. https://doi.org/10.1371/journal.pone.0001406

Wiggins, P. M. and van Ryn, R. T. (1986). The solvent properties of water in desalination membranes. J. Macromol. Sci. Chem. A23: 875-903.

What is claimed is:

1. A method for the desalination of seawater comprising the steps of:
    arranging two glass Petri dishes of equal diameter, as upper and lower dishes;
    placing seawater into each Petri dish; and
    extracting melanin from a culture of treated *Aspergillus niger*, washed and dried to form a melanin powder;
    adding 0.17 gm of the melanin powder per 10 ml of water to the lower dish and the set is exposed to light indoors.

2. The method for the desalination of seawater of claim 1, wherein the obtained droplets of fresh water is collected from the lower surface of the upper dish.

3. A method for the desalination of seawater comprising the steps of:
    utilizing plastic containers of the same size arranged as upper and lower compartments;
    placing a volume of 600 ml seawater into each plastic container;
    extracting melanin from a culture of treated *Aspergillus niger*, washed and dried to form a melanin powder;
    adding 0.17 gm of the melanin powder per 10 ml of water in the lower compartment; and
    exposing the plastic containers outdoors under direct sunlight.

4. The method of desalination of seawater of claim 3, wherein the obtained droplets fresh water is collected from the lower surface of the upper container.

* * * * *